US008865932B2

(12) United States Patent
Zhou et al.

(10) Patent No.: US 8,865,932 B2
(45) Date of Patent: Oct. 21, 2014

(54) FLUORINATED GRAPHENE OXIDE AND PREPARATION METHOD THEREOF

(75) Inventors: Mingjie Zhou, Shenzhen (CN); Daxi Liu, Shenzhen (CN); Yaobing Wang, Shenzhen (CN)

(73) Assignee: Ocean's King Lighting Science & Technology Co., Ltd., Shenzhen, Guangdong (CN)

( * ) Notice: Subject to any disclaimer, the term of this patent is extended or adjusted under 35 U.S.C. 154(b) by 47 days.

(21) Appl. No.: 13/988,287

(22) PCT Filed: Dec. 22, 2010

(86) PCT No.: PCT/CN2010/080127
§ 371 (c)(1),
(2), (4) Date: May 17, 2013

(87) PCT Pub. No.: WO2012/083534
PCT Pub. Date: Jun. 28, 2012

(65) Prior Publication Data
US 2013/0237723 A1 Sep. 12, 2013

(51) Int. Cl.
*C07C 51/16* (2006.01)
*C07C 51/255* (2006.01)
*C01B 31/04* (2006.01)
*C07C 51/305* (2006.01)
*C07C 65/24* (2006.01)

(52) U.S. Cl.
CPC ............ *C07C 65/24* (2013.01); *C01B 31/043* (2013.01); *C07C 51/305* (2013.01)
USPC ...................................... 562/408

(58) Field of Classification Search
CPC .... C07C 51/265; C07C 51/313; C07C 51/43; C07C 51/31
See application file for complete search history.

(56) References Cited

U.S. PATENT DOCUMENTS

| 2007/0231696 A1* | 10/2007 | Yazami et al. .......... 429/231.7 |
| 2008/0048152 A1 | 2/2008 | Jang et al. |
| 2008/0206124 A1 | 8/2008 | Jang et al. |
| 2010/0222482 A1 | 9/2010 | Jang et al. |

FOREIGN PATENT DOCUMENTS

| CN | 101486454 A | 7/2009 |
| JP | H06212110 A | 8/1994 |
| JP | H08250117 A | 9/1996 |

OTHER PUBLICATIONS

Edna et al. (Advanced Materials, 2010, 22(22), 2392).*
Tsuyoshi Nakajim and Yoshiaki Matsuo, Formation Process and Structure of Graphite Oxide, Carbon. vol. 32 No. 3. pp. 469-475. 1994.
Franklin Kim, et al, Self-propagating Domino-like Reactions in Oxidized Graphite. Adv, Funct. Mater. 2010, 20, 2867-2873.

* cited by examiner

*Primary Examiner* — Rosalynd Keys
*Assistant Examiner* — Jennifer C Sawyer
(74) *Attorney, Agent, or Firm* — Shimokaji & Associates, P.C.

(57) ABSTRACT

Provided are a fluorinated graphene oxide and a preparation method thereof. In the fluorinated graphene oxide, the mass percent of fluorine is 0.5%<F %<40%; the mass percent of carbon is 50%<C %<80%, and the mass percent of oxygen is 0.5%<O %<30%. The preparation method comprises the following steps: providing graphite; preparing graphene oxide by using the graphite; and subjecting the graphene oxide to reacting with a mixed gas of $N_2$ and $F_2$ at 20~200° C. for 0.5~24 h, to prepare the fluorinated graphene oxide. The preparation method is simple, has fewer steps, and has better prospect of application.

20 Claims, 1 Drawing Sheet

FLUORINATED GRAPHENE OXIDE AND PREPARATION METHOD THEREOF

FIELD OF THE INVENTION

The present invention relates to the field of organic semiconductor materials technique, more particularly, the present invention relates to fluorinated graphene oxide and preparation method thereof.

BACKGROUND OF THE INVENTION

Since Andre K. Geim and co-workers at Manchester University in the United Kingdom successfully produced graphene material in 2004, graphene material has attracted considerable attention owing to its unique structure and photoelectrical properties. Graphene is considered as a "rising star" in the field of materials science and condensed matter physics. It has attracted intensive attention because of its unique and potential technical applications. Single-layer graphene has large specific surface area, excellent electrical conductivity, thermal conductivity, low coefficient of thermal expansion. Such as: 1, high strength, Young's modulus (1100 GPa), breaking strength (125 GPa); 2, high thermal conductivity, thermal conductivity coefficient (5,000 W/mK); 3, high electrical conductivity, the transmission rate of carriers (200,000 $cm^2/V*s$); 4, large specific surface area, (the theoretical value: 2,630 $m^2/g$). Especially for its high electrical conductivity, large specific surface area and single-layer planar nanoscale structure, it can be used as electrode materials of super capacitor and lithium-ion battery.

Graphene oxide exhibits strong polarity due to its —C—OH, —C—O—C, —COOH groups. Dry graphene oxide shows poor stability when stays in the air, and tends to absorb moisture to form hydrated graphite oxide. However, graphite oxide can be provided with improved stability after being fluorinated to form fluorinated graphene oxide. As electrode materials, the discharge capacity of fluorinated graphite oxide is much greater than that of graphite oxide, especially fluorinated graphene oxide produced at 110° C. by reacting with $F_2$, discharge capacity and energy density can reach 675 mA h/g and 1420 W h/Kg respectively when discharge current density is 0.5 $mA/cm^2$ (1M $LiClO_4$—PC).

However, how to obtain fluorographene by an easy method is a difficult problem still existing nowadays.

SUMMARY OF THE INVENTION

In view of this, it is necessary to provide at least one preparation method of fluorinated graphene oxide having simple process, and fluorinated graphene oxide produced by the above-mentioned preparation method of fluorinated graphene oxide.

Fluorinated graphene oxide, mass percent of fluorine is in the range of 0.5%<F %<40%, mass percent of carbon is in the range of 50%<C %<80%, mass percent of oxygen is in the range of 0.5%<O %<30%.

Preferably, mass percent of fluorine is in the range of 9%<F %<27%, mass percent of carbon is in the range of 55%<C %<75%, mass percent of oxygen is in the range of 18%<O %<27%.

A preparation method of fluorinated graphene oxide, comprising:
providing graphite;
preparing graphene oxide by using said graphite;
obtaining said fluorinated graphene oxide by reacting graphene oxide with mixed gases of $N_2$ and $F_2$ at reaction temperature 20~200° C. for 0.5~24 h.

Preferably, in said mixed gases, volume percent of $F_2$ is in the range of 5~30%.

Preferably, in said mixed gases, volume percent of $F_2$ is in the range of 8~25%.

Preferably, in said mixed gases, volume percent of $F_2$ is 20%.

Preferably, in said mixed gases, volume percent of $F_2$ is 10%.

Preferably, reaction temperature is in the range of 50~150° C., reaction time is in the range of 2~20 h.

Preferably, the step of preparing graphene oxide by using said graphite comprises:

adding said graphite, potassium persulfate and phosphorus pentoxide by mass ratio of 2:1:1 into concentrated sulfuric acid at 60~85° C., stirring well and then cooling naturally, washing to neutrality, then drying to obtain pretreated mixture;

adding said pretreated mixture and potassium permanganate into concentrated sulfuric acid below 20° C., then heating in an oil-bath at 30~40° C. for 1.5~2.5 h, adding deionized water, after 15 minutes, adding hydrogen peroxide to react, filtrating by applying pressure, collecting solid;

washing said solid with diluted hydrochloric acid, drying to obtain said graphene oxide.

Preferably, degree of purity of said graphite is higher than 99.5%.

The above-mentioned preparation method of fluorinated graphene oxide involves preparing graphene oxide with graphite, then reacting graphene oxide with mixed gases of $N_2$ and $F_2$ at a certain temperature to produce fluorinated graphene oxide. This preparation method of fluorinated graphene oxide has fewer steps, simple process and better prospect of application.

DETAILED DESCRIPTION OF ILLUSTRATED EMBODIMENTS

Further description of fluorinated graphene oxide and preparation method thereof will be illustrated, which combined with embodiments and the drawings.

Fluorinated graphene oxide, mass percent of fluorine is in the range of 0.5%<F %<40%, mass percent of carbon is in the range of 50%<C %<80%, mass percent of oxygen is in the range of 0.5%<O %<30%.

In one preferred embodiment, mass percent of fluorine is in the range of 9%<F %<27%, mass percent of carbon is in the range of 55%<C %<75%, mass percent of oxygen is in the range of 18%<O %<27%.

Figure 1:
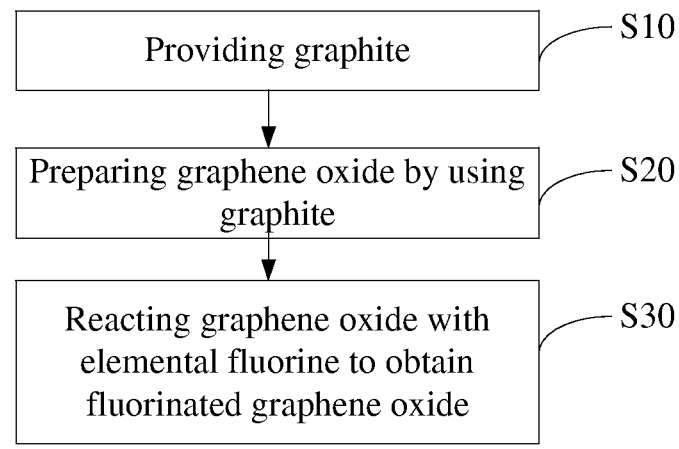
FIG. 1 is a flow chart of preparation method of fluorinated graphene oxide of one embodiment.
Figure 2:
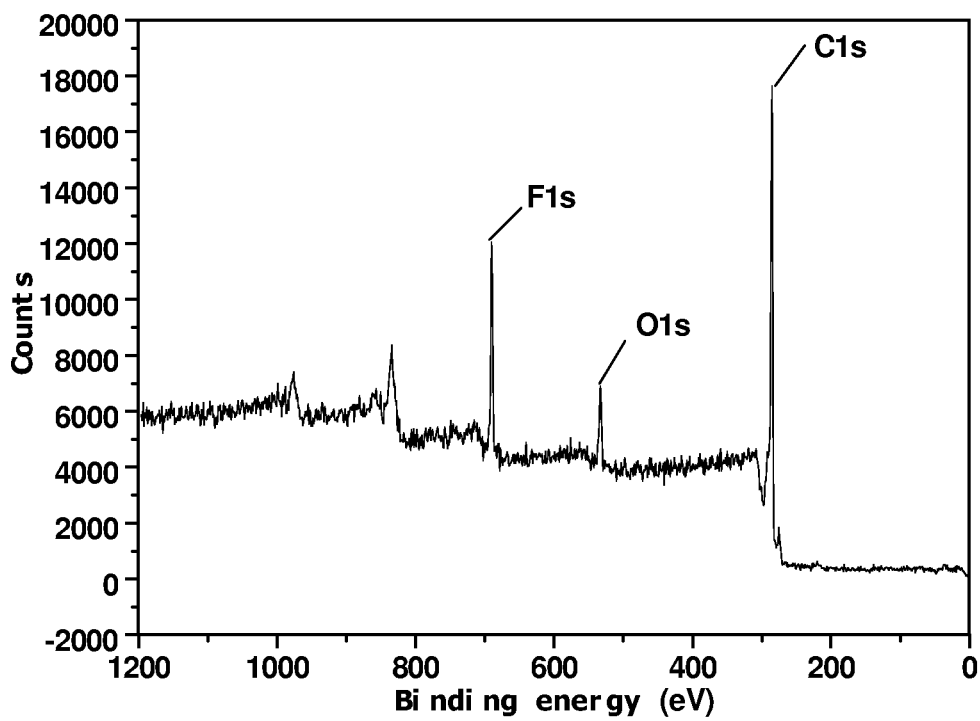
FIG. 2 is a wide-scan survey spectrum of XPS for C1s, O1s and F1s of fluorinated graphene oxide of the Example 1.

As shown in FIG. 1, a preparation method of fluorinated graphene oxide, comprising:

S10, providing graphite;

Graphite having degree of purity higher than 99.5% is purchased.

S20, preparing graphene oxide by using graphite;

Normally, graphite oxide can be prepared by Hummers method, which comprises: placing graphite, potassium permanganate and concentrated strong oxidizing acid (sulfuric acid or nitric acid) into the same container for heating by water-bath or oil-bath, fully oxidizing then taking out, reducing potassium permanganate with hydrogen peroxide firstly, then washing the products with distilled water or hydrochloric acid for many times, drying to obtain graphite oxide.

In order to prepare graphene oxide, Hummers method can be improved, the improved preparation method comprises the following steps.

Firstly, adding graphite, potassium persulfate and phosphorus pentoxide by mass ratio of 2:1:1 into concentrated sulfuric acid at 60~85° C., stirring well and then cooling naturally, washing to neutrality, then drying to obtain pretreated mixture.

Secondly, adding said pretreated mixture and potassium permanganate into concentrated sulfuric acid, keeping the temperature below 20° C., then heating in an oil-bath at 30~40° C. for 1.5~2.5 h, adding deionized water, after 15 minutes, adding hydrogen peroxide to react, filtrating by applying pressure, collecting solid.

At last, washing the solid with diluted hydrochloric acid, drying to obtain said graphene oxide.

The purpose of heating by oil-bath is to control reaction temperature more easily. In other embodiments, water-bath can also be used.

S30, obtaining fluorinated graphene oxide by reacting graphene oxide with elemental fluorine.

The method involving producing fluorinated graphene oxide by the reaction of graphene oxide obtained from step S20 with elemental fluorine ($F_2$) is called solid-phase method, mixed gases of $N_2$ and $F_2$ are employed, and specific steps are as follows:

Placing the dried graphene oxide obtained from step S20 into reactor with supplying mixed gases of $N_2$ and $F_2$ (volume percent of $F_2$ is in the range of 5%~30%), keeping the temperature at 20~200° C., reacting for 0.5~24 h to react graphene oxide with $F_2$. F partially substitutes for O to produce fluorinated graphene oxide.

In one preferred embodiment, volume percent of $F_2$ in mixed gases is in the range of 8~25%, reaction temperature is in the range of 50~150° C., reaction time is in the range of 2~20 h.

In one further preferred embodiment, volume percent of $F_2$ in mixed gases is 10% or 20%.

The above-mentioned preparation method of fluorinated graphene oxide involves preparing graphene oxide with graphite, then obtaining fluorinated graphene oxide by reacting graphene oxide with mixed gases of $N_2$ and $F_2$. This preparation method of fluorinated graphene oxide has fewer steps, simpler process and better prospect of application.

The obtained fluorinated graphene oxide can be used as electrode materials of super capacitor and lithium-ion secondary battery.

The present invention will be described below in detail referring to preferred embodiments.

Example 1

In the present embodiment, the process of preparing fluorinated graphene oxide by using graphene oxide was:
graphite→graphene oxide→fluorinated graphene oxide
(1) Graphite: degree of purity was 99.5%
(2) Graphene oxide: graphene oxide was prepared using improved Hummers method, comprising: adding 20 g of 50-mesh sieved graphite powders, 10 g of potassium persulfate and 10 g of phosphorus pentoxide into concentrated sulfuric acid at 80° C., stirring well, cooling for more than 6 h, washing to neutrality, drying; adding the samples as dried into 230 mL of concentrated sulfuric acid at 0° C., then adding 60 g of potassium permanganate, keeping the temperature of mixture below 20° C., then heating in an oil-bath at 35° C. and maintaining for 2 h, after that, adding slowly 920 mL of deionized water, after 15 minutes, adding 2.8 L of deionized water (containing 50 mL of hydrogen peroxide having concentration of 30%), subsequently, the color of mixture became bright yellow, filtrating by applying pressure while the mixture was hot, then washing with 5 L of hydrochloric acid having concentration of 10%, filtrating by applying pressure, vacuum drying at 60° C. for 48 h to obtain graphene oxide.

(3) Fluorinated graphene oxide: fluorinated graphene oxide was prepared by reacting graphene oxide obtained from (2) with $F_2$, comprising the following steps: placing dried graphene oxide into reactor and supplying dry $N_2$ for 2 h, then supplying mixed gases of fluorine and nitrogen in which the volume percent of fluorine was 10%, reacting with graphene oxide at 100° C. for 12 h, then obtaining fluorinated graphene oxide.

The following test was performed on the obtained fluorinated graphene:

Experimental conditions of XPS test: samples were analyzed with ESCALab220i-XL X-ray photoelectron spectroscopy from VG Scientific using roughly 300 W Al Kα X-ray radiation. The base pressure was at $3 \times 10^{-9}$ mbar when analyzing. The binding energies were referenced to the C1s line at 284.8 eV from adventitious carbon.

Relative quantity of element is given by $$\text{Relative atomic percent} = \frac{\frac{I_i}{S_i}}{\sum \frac{I_i}{S_i}} \times 100\%$$

where $I_i$—peak intensity (area) of element i
$S_i$—relative sensitivity factor of element i Tab. 1 indicated that mass percent of F was 40%, mass percent of oxygen was 15%.

FIG. 3 is a wide-scan survey spectrum of XPS for C1s, O1s and F1s of fluorinated graphene oxide of the present embodiment.

It can be seen from the figure that a strong peak appears at 284.8 eV which represents C—C (284.8 eV), the hydrocarbon moieties of fluorographene as prepared.

A strong peak appears at 533.0 eV which represents C—O (533.0 eV), the hydrocarbon moieties of fluorographene as prepared.

A strong peak appears at 689.5 eV which represents C—F (689.5 eV), the hydrocarbon moieties of fluorographene as prepared.

Example 2

In the present embodiment, the process of preparing fluorinated graphene oxide by using graphene oxide was:
graphite→graphene oxide→fluorinated graphene oxide
(1) Graphite: degree of purity was 99.5%
(2) Graphene oxide: graphene oxide was prepared using improved Hummers method, comprising: adding 20 g of 50-mesh sieved graphite powders, 10 g of potassium persulfate and 10 g of phosphorus pentoxide into concentrated sulfuric acid at 75° C., stirring well, cooling for more than 6 h, washing to neutrality, drying; adding the samples as dried into 230 mL of concentrated sulfuric acid at 0° C., then adding 60 g of potassium permanganate, keeping the temperature of mixture below 20° C., then heating in an oil-bath at 40° C. and maintaining for 2.5 h, after that, adding slowly 920 mL of deionized water, after 15 minutes, adding 2.8 L of deionized water (containing 50 mL of hydrogen peroxide having concentration of 30%), subsequently, the color of mixture became bright yellow, filtrating by applying pressure while the mixture was hot, then washing with 5 L of hydrochloric acid having concentration of 10%, filtrating by applying pressure, vacuum drying at 60° C. for 48 h to obtain graphene oxide.

(3) Fluorinated graphene oxide: fluorinated graphene oxide was prepared by reacting graphene oxide obtained from (2) with $F_2$, comprising the following steps: placing dried graphene oxide into reactor and supplying dry $N_2$ for 4 h, then supplying mixed gases of fluorine and nitrogen in which the volume percent of fluorine was 5%, reacting with graphene oxide at 20° C. for 24 h, then obtaining fluorinated graphene oxide.

Tab. 1 indicated that mass percent of F was 27%, mass percent of oxygen was 18%.

Example 3

In the present embodiment, the process of preparing fluorinated graphene oxide by using graphene oxide was:

graphite→graphene oxide→fluorinated graphene oxide (1) Graphite: degree of purity was 99.5%

(2) Graphene oxide: graphene oxide was prepared using improved Hummers method, comprising: adding 20 g of 50-mesh sieved graphite powders, 10 g of potassium persulfate and 10 g of phosphorus pentoxide into concentrated sulfuric acid at 95° C., stirring well, cooling for more than 6 h, washing to neutrality, drying; adding the samples as dried into 230 mL of concentrated sulfuric acid at 0° C., then adding 60 g of potassium permanganate, keeping the temperature of mixture below 20° C., then heating in an oil-bath at 30° C. and maintaining for 1.5 h, after that, adding slowly 920 mL of deionized water, after 15 minutes, adding 2.8 L of deionized water (containing 50 mL of hydrogen peroxide having concentration of 30%), subsequently, the color of mixture became bright yellow, filtrating by applying pressure while the mixture was hot, then washing with 5 L of hydrochloric acid having concentration of 10%, filtrating by applying pressure, vacuum drying at 60° C. for 48 h to obtain graphene oxide.

(3) Fluorinated graphene oxide: fluorinated graphene oxide was prepared by reacting graphene oxide obtained from (2) with $F_2$, comprising the following steps: placing dried graphene oxide into reactor and supplying dry $N_2$ for 0.5 h, then supplying mixed gases of fluorine and nitrogen in which the volume percent of fluorine was 30%, reacting with graphene oxide at 50° C. for 24 h, then obtaining fluorinated graphene oxide.

Tab. 1 indicated that mass percent of F was 16%, mass percent of oxygen was 27%.

Example 4

In the present embodiment, the process of preparing fluorinated graphene oxide by using graphene oxide was:

graphite→graphene oxide→fluorinated graphene oxide (1) Graphite: degree of purity was 99.5%

(2) Graphene oxide: graphene oxide was prepared using improved Hummers method, comprising: adding 20 g of 50-mesh sieved graphite powders, 10 g of potassium persulfate and 10 g of phosphorus pentoxide into concentrated sulfuric acid at 85° C., stirring well, cooling for more than 6 h, washing to neutrality, drying; adding the samples as dried into 230 mL of concentrated sulfuric acid at 0° C., then adding 60 g of potassium permanganate, keeping the temperature of mixture below 20° C., then heating in an oil-bath at 35° C. and maintaining for 2 h, after that, adding slowly 920 mL of deionized water, after 15 minutes, adding 2.8 L of deionized water (containing 50 mL of hydrogen peroxide having concentration of 30%), subsequently, the color of mixture became bright yellow, filtrating by applying pressure while the mixture was hot, then washing with 5 L of hydrochloric acid having concentration of 10%, filtrating by applying pressure, vacuum drying at 60° C. for 48 h to obtain graphene oxide.

(3) Fluorinated graphene oxide: fluorinated graphene oxide was prepared by reacting graphene oxide obtained from (2) with $F_2$, comprising the following steps: placing dried graphene oxide into reactor and supplying dry $N_2$ for 3 h, then supplying mixed gases of fluorine and nitrogen in which the volume percent of fluorine was 20%, reacting with graphene oxide at 200° C. for 0.5 h, then obtaining fluorinated graphene oxide.

Tab. 1 indicated that mass percent of F was 15%, mass percent of oxygen was 29%.

Example 5

In the present embodiment, the process of preparing fluorinated graphene oxide by using graphene oxide was:

graphite→graphene oxide→fluorinated graphene oxide (1) Graphite: degree of purity was 99.5%

(2) Graphene oxide: graphene oxide was prepared using improved Hummers method, comprising: adding 20 g of 50-mesh sieved graphite powders, 10 g of potassium persulfate and 10 g of phosphorus pentoxide into concentrated sulfuric acid at 80° C., stirring well, cooling for more than 6 h, washing to neutrality, drying; adding the samples as dried into 230 mL of concentrated sulfuric acid at 0° C., then adding 60 g of potassium permanganate, keeping the temperature of mixture below 20° C., then heating in an oil-bath at 35° C. and maintaining for 2 h, after that, adding slowly 920 mL of deionized water, after 15 minutes, adding 2.8 L of deionized water (containing 50 mL of hydrogen peroxide having concentration of 30%), subsequently, the color of mixture became bright yellow, filtrating by applying pressure while the mixture was hot, then washing with 5 L of hydrochloric acid having concentration of 10%, filtrating by applying pressure, vacuum drying at 60° C. for 48 h to obtain graphene oxide.

(3) Fluorinated graphene oxide: fluorinated graphene oxide was prepared by reacting graphene oxide obtained from (2) with $F_2$, comprising the following steps: placing dried graphene oxide into reactor and supplying dry $N_2$ for 2 h, then supplying mixed gases of fluorine and nitrogen in which the volume percent of fluorine was 8%, reacting with graphene oxide at 120° C. for 10 h, then obtaining fluorinated graphene oxide.

Tab. 1 indicated that mass percent of F was 9%, mass percent of oxygen was 25%.

Example 6

In the present embodiment, the process of preparing fluorinated graphene oxide by using graphene oxide was:

graphite→graphene oxide→fluorinated graphene oxide (1) Graphite: degree of purity was 99.5%

(2) Graphene oxide: graphene oxide was prepared using improved Hummers method, comprising: adding 20 g of 50-mesh sieved graphite powders, 10 g of potassium persulfate and 10 g of phosphorus pentoxide into concentrated sulfuric acid at 80° C., stirring well, cooling for more than 6 h, washing to neutrality, drying; adding the samples as dried into 230 mL of concentrated sulfuric acid at 0° C., then adding 60 g of potassium permanganate, keeping the temperature of mixture below 20° C., then heating in an oil-bath at 35° C. and maintaining for 2 h, after that, adding slowly 920 mL of deionized water, after 15 minutes, adding 2.8 L of deionized water (containing 50 mL of hydrogen peroxide having concentration of 30%), subsequently, the color of mixture became bright yellow, filtrating by applying pressure while the mixture was hot, then washing with 5 L of hydrochloric acid having concentration of 10%, filtrating by applying pressure, vacuum drying at 60° C. for 48 h to obtain graphene oxide.

(3) Fluorinated graphene oxide: fluorinated graphene oxide was prepared by reacting graphene oxide obtained from (2) with $F_2$, comprising the following steps: placing dried graphene oxide into reactor and supplying dry $N_2$ for 2 h, then supplying mixed gases of fluorine and nitrogen in which the volume percent of fluorine was 25%, reacting with graphene oxide at 80° C. for 4 h, then obtaining fluorinated graphene oxide.

Tab. 1 indicated that mass percent of F was 0.5%, mass percent of oxygen was 30%.

TABLE 1 contents of F and O of fluorinated graphene oxide

| No. | Example 1 | Example 2 | Example 3 | Example 4 | Example 5 | Example 6 |
|---|---|---|---|---|---|---|
| F content | 40% | 27% | 16% | 15% | 9% | 0.5% |
| O content | 15% | 18% | 27% | 29% | 25% | 30% |

While the present invention has been described with reference to particular embodiments, it will be understood that the embodiments are illustrative and that the invention scope is not so limited. Alternative embodiments of the present invention will become apparent to those having ordinary skill in the art to which the present invention pertains. Such alternate embodiments are considered to be encompassed within the spirit and scope of the present invention. Accordingly, the scope of the present invention is described by the appended claims and is supported by the foregoing description.

What is claimed is:

1. Fluorinated graphene oxide, wherein, mass percent of fluorine is in the range of 0.5%<F %<40%, mass percent of carbon is in the range of 50%<C %<80%, mass percent of oxygen is in the range of 0.5%<O %<30%.

2. The fluorinated graphene oxide as claimed in claim 1, wherein, mass percent of fluorine is in the range of 9%<F %<27%, mass percent of carbon is in the range of 55%<C %<75%, mass percent of oxygen is in the range of 18%<O %<27%.

3. A preparation method of fluorinated graphene oxide, wherein, comprising:
providing graphite;
preparing graphene oxide by using said graphite;
obtaining said fluorinated graphene oxide by reacting graphene oxide with mixed gases of $N_2$ and $F_2$ at reaction temperature 20~200° C. for 0.5~24 h.

4. The preparation method of fluorinated graphene oxide as claimed in claim 3, wherein in said mixed gases, volume percent of $F_2$ is in the range of 5~30%.

5. The preparation method of fluorinated graphene oxide as claimed in claim 4, wherein in said mixed gases, volume percent of $F_2$ is in the range of 8~25%.

6. The preparation method of fluorinated graphene oxide as claimed in claim 5, wherein in said mixed gases, volume percent of $F_2$ is 20%.

7. The preparation method of fluorinated graphene oxide as claimed in claim 5, wherein in said mixed gases, volume percent of $F_2$ is 10%.

8. The preparation method of fluorinated graphene oxide as claimed in claim 3, wherein reaction temperature is in the range of 50~150° C., reaction time is in the range of 2~20 h.

9. The preparation method of fluorinated graphene oxide as claimed in claim 3, the step of preparing graphene oxide by using said graphite comprises:
adding said graphite, potassium persulfate and phosphorus pentoxide by mass ratio of 2:1:1 into concentrated sulfuric acid at 60~85° C., stirring well and then cooling naturally, washing to neutrality, then drying to obtain pretreated mixture;
adding said pretreated mixture and potassium permanganate into concentrated sulfuric acid below 20° C., then heating in an oil-bath at 30~40° C. for 1.5~2.5 h, adding deionized water, after 15 minutes, adding hydrogen peroxide to react, filtrating by applying pressure, collecting solid;
washing said solid with diluted hydrochloric acid, drying to obtain said graphene oxide.

10. The preparation method of fluorinated graphene oxide as claimed in claim 3, wherein, degree of purity of said graphite is higher than 99.5%.

11. The preparation method of fluorinated graphene oxide as claimed in claim 4, the step of preparing graphene oxide by using said graphite comprises:
adding said graphite, potassium persulfate and phosphorus pentoxide by mass ratio of 2:1:1 into concentrated sulfuric acid at 60~85° C., stirring well and then cooling naturally, washing to neutrality, then drying to obtain pretreated mixture;
adding said pretreated mixture and potassium permanganate into concentrated sulfuric acid below 20° C., then heating in an oil-bath at 30~40° C. for 1.5~2.5 h, adding deionized water, after 15 minutes, adding hydrogen peroxide to react, filtrating by applying pressure, collecting solid;
washing said solid with diluted hydrochloric acid, drying to obtain said graphene oxide.

12. The preparation method of fluorinated graphene oxide as claimed in claim 5, the step of preparing graphene oxide by using said graphite comprises:
adding said graphite, potassium persulfate and phosphorus pentoxide by mass ratio of 2:1:1 into concentrated sulfuric acid at 60~85° C., stirring well and then cooling naturally, washing to neutrality, then drying to obtain pretreated mixture;
adding said pretreated mixture and potassium permanganate into concentrated sulfuric acid below 20° C., then heating in an oil-bath at 30~40° C. for 1.5~2.5 h, adding deionized water, after 15 minutes, adding hydrogen peroxide to react, filtrating by applying pressure, collecting solid;
washing said solid with diluted hydrochloric acid, drying to obtain said graphene oxide.

13. The preparation method of fluorinated graphene oxide as claimed in claim 6, the step of preparing graphene oxide by using said graphite comprises:
- adding said graphite, potassium persulfate and phosphorus pentoxide by mass ratio of 2:1:1 into concentrated sulfuric acid at 60~85° C., stirring well and then cooling naturally, washing to neutrality, then drying to obtain pretreated mixture;
- adding said pretreated mixture and potassium permanganate into concentrated sulfuric acid below 20° C., then heating in an oil-bath at 30~40° C. for 1.5~2.5 h, adding deionized water, after 15 minutes, adding hydrogen peroxide to react, filtrating by applying pressure, collecting solid;
- washing said solid with diluted hydrochloric acid, drying to obtain said graphene oxide.

14. The preparation method of fluorinated graphene oxide as claimed in claim 7, the step of preparing graphene oxide by using said graphite comprises:
- adding said graphite, potassium persulfate and phosphorus pentoxide by mass ratio of 2:1:1 into concentrated sulfuric acid at 60~85° C., stirring well and then cooling naturally, washing to neutrality, then drying to obtain pretreated mixture;
- adding said pretreated mixture and potassium permanganate into concentrated sulfuric acid below 20° C., then heating in an oil-bath at 30~40° C. for 1.5~2.5 h, adding deionized water, after 15 minutes, adding hydrogen peroxide to react, filtrating by applying pressure, collecting solid;
- washing said solid with diluted hydrochloric acid, drying to obtain said graphene oxide.

15. The preparation method of fluorinated graphene oxide as claimed in claim 8, the step of preparing graphene oxide by using said graphite comprises:
- adding said graphite, potassium persulfate and phosphorus pentoxide by mass ratio of 2:1:1 into concentrated sulfuric acid at 60~85° C., stirring well and then cooling naturally, washing to neutrality, then drying to obtain pretreated mixture;
- adding said pretreated mixture and potassium permanganate into concentrated sulfuric acid below 20° C., then heating in an oil-bath at 30~40° C. for 1.5~2.5 h, adding deionized water, after 15 minutes, adding hydrogen peroxide to react, filtrating by applying pressure, collecting solid;
- washing said solid with diluted hydrochloric acid, drying to obtain said graphene oxide.

16. The preparation method of fluorinated graphene oxide as claimed in claim 4, wherein, degree of purity of said graphite is higher than 99.5%.

17. The preparation method of fluorinated graphene oxide as claimed in claim 5, wherein, degree of purity of said graphite is higher than 99.5%.

18. The preparation method of fluorinated graphene oxide as claimed in claim 6, wherein, degree of purity of said graphite is higher than 99.5%.

19. The preparation method of fluorinated graphene oxide as claimed in claim 7, wherein, degree of purity of said graphite is higher than 99.5%.

20. The preparation method of fluorinated graphene oxide as claimed in claim 8, wherein, degree of purity of said graphite is higher than 99.5%.

* * * * *